United States Patent [19]

Green et al.

[11] Patent Number: 5,525,336

[45] Date of Patent: Jun. 11, 1996

[54] COSMETIC CONTAINING CORNEOCYTE PROTEINS AND TRANSGLUTAMINASE, AND METHOD OF APPLICATION

[76] Inventors: Howard Green, 82 Williston Rd., Brookline, Mass. 02146; Philippe Dijan, 18, rue Ferdinand Fabre 75015, Paris, France

[21] Appl. No.: 245,601

[22] Filed: May 18, 1994

Related U.S. Application Data

[62] Division of Ser. No. 20,212, Feb. 19, 1993, abandoned.

[51] Int. Cl.$^6$ ............................ A61K 38/53; C12P 21/06; C12N 9/10
[52] U.S. Cl. .................. 424/94.5; 424/418; 435/68.1; 435/193; 514/2
[58] Field of Search .............................. 514/2; 424/94.5, 424/418; 435/193, 68.1; 530/350

[56] References Cited

U.S. PATENT DOCUMENTS

| | | | |
|---|---|---|---|
| 4,279,996 | 7/1981 | Yoshioka et al. | 435/68.1 |
| 4,338,214 | 7/1982 | Fischer et al. | 252/545 |
| 4,369,037 | 1/1983 | Matsunaga et al. | 8/127.51 |
| 4,517,175 | 5/1985 | Iwabuchi et al. | 424/70 |
| 4,699,778 | 10/1987 | Marty | 424/59 |
| 4,705,682 | 11/1987 | Moeller et al. | 424/70 |
| 4,832,946 | 5/1989 | Green | 424/70 |
| 4,839,168 | 6/1989 | Abe et al. | 424/74 |
| 4,879,116 | 11/1989 | Fox et al. | 424/682 |
| 4,885,169 | 12/1989 | Gazzani | 424/104 |
| 4,973,473 | 11/1990 | Schneider et al. | 424/63 |
| 5,080,888 | 1/1992 | Grollier et al. | 424/61 |
| 5,091,173 | 2/1992 | Buultjens et al. | 424/70 |
| 5,100,956 | 3/1992 | O'Lenick, Jr. | 525/54.1 |
| 5,135,913 | 8/1992 | Pickart | 514/16 |

FOREIGN PATENT DOCUMENTS

| | | |
|---|---|---|
| 13742 | 9/1988 | Australia . |
| 0285474 | 10/1988 | European Pat. Off. . |
| 0481504A1 | 10/1991 | European Pat. Off. . |
| 0511116 | 10/1992 | European Pat. Off. . |
| 61-172807 | 8/1986 | Japan . |
| 2-204407 | 8/1990 | Japan . |
| 3-38511 | 2/1991 | Japan . |
| 5-56785 | 3/1991 | Japan . |
| WO92/12238 | 7/1992 | WIPO . |

OTHER PUBLICATIONS

Rialdi et al. (1988) *Cosmetics & Toiletries*, 103, 89–94.
Simon et al. (1985) *Cell*, 40, 677–683.
Etoh et al. (1986) *Biochem. Biophys. Res. Comm.* 136(1), 51–56.
Mehrel et al. (1990) *Cell*, 6, 1103–1112.
Greenberg et al. (1991) *FASEB J*, 5, 3071–3077.
Kvedar et al. (1992) *Differentiation*, 49, 195–204.
Fietz et al. (1990) *J. Cell Biol.*, 110, 427–436.
Highley (1984) *Cosmetics & Toiletries*, 99, 57–62.
Steven, M. and P. Steinert, J. Cell Science 107:693–700 (1994).
Tabor H. and C. Tabor, Eds., Methods in Enzymology, vol. 17A, 1970, pp. 889–894.
Banks–Schlegel, "Involucrin Synthesis and Tissue Assembly By Keratinocytes in Natural and Cultured Human Epithelia", *J. of Cell Biology*, 90:732, 737 (1981).
Eckert, "Structure and Evolution of the Human Involucrin Gene", *Cell*, 46:583–589 (1986).
Green, "Terminal Differentiation of Cultured Human Epidermal Cells" *Cell*, 11:405–416 (1977).
Hohl. "Cornified Cell Envelope", *Dermatologica*, 1809: 201–211 (1990).
Hohl, "Characterization of Human Loricrin", *The J. of Biological Chemistry*, 266:6626–6636 (1991).
Markova, "Profilaggrin Is a Major Epiderman Calcium–Binding Protein", *Molecular And Cellular Biology*, 13:613–625 (1993).
Marvin, "Cornifin, a Cross–Linked Envelope Precursor In Keratinocytes That Is Down–Regulated By Retinoids", *Biochemistry*, 89:11026–11030 (1992).
Phillips, "Primary Structure of Keratinocyte Transglutaminase", *Biochemistry*, 87:9333–9337 (1990).
Rice, "Presence in Human Epidermal Cells of a Soluble Protein Precursor of the Cross–Linked Envelope: Activation of the Cross–Linking by Calcium Ions", *Cell*, 18:681–694 (1979).
Rice, "The Cornified Envelope of Terminally Differentiated Human Epidermal Keratinocytes Consists of Cross–Linked Protein", *Cell*, 11:417–422 (1977).
Steven, "Biosynthetic Pathways of Filaggrin And Loricrin— Two Major Proteins Expressed By Terminally Differentiated Epidermal Keratinocytes", *J. of Structural Biology*, 104:150–162 (1990).
Rialdi et al., "Filaggrin Overview; Functions and Cosmetic Aim", *Cosmetics & Toiletries*, 103:89–94 (1988).
(Abstract) *Women's Wear Daily*, p. 6, (Oct. 9, 1992).

*Primary Examiner*—David M. Naff
*Assistant Examiner*—Jon P. Weber
*Attorney, Agent, or Firm*—Wolf, Greenfield & Sacks

[57] ABSTRACT

A cosmetic composition comprising corneocyte proteins and transglutaminase in a cosmetically acceptable vehicle is provided. Upon application, the ingredients of the cosmetic cross link with the outer layer of skin, hair or nails to form a protective layer on the skin, hair or nails.

16 Claims, 1 Drawing Sheet

COSMETIC CONTAINING CORNEOCYTE PROTEINS AND TRANSGLUTAMINASE, AND METHOD OF APPLICATION

This is a divisional of application Ser. No. 08/020,212 filed on Feb. 19, 1993 now abandoned.

BACKGROUND OF THE INVENTION

The epidermis is a stratified epithelium consisting of numerous cell layers. The principal cell type of the epidermis is the keratinocyte. Keratinocytes are responsible for the resistance of the skin to physical and chemical injury and for its impermeability to water. These functions are carried out primarily by the outermost layer of keratinocytes, termed "corneocytes," which have undergone programmed cell death. Corneocytes consist of a skeletal framework of keratin filaments surrounded by a special envelope that is found in no other cells within the body. This envelope consists of proteins ("corneocyte proteins") stabilized by inter-molecular isopeptide bonds (Rice and Green (1977), *Cell*, 11:417–422). The bonds are introduced by an enzyme, calcium-activated keratinocyte transglutaminase (Rice and Green (1979), *Cell*, 18:681–694). As skin ages, the epidermis atrophies with accompanying diminution of its physical resistance.

The basal layer of the epidermis contains proliferating keratinocytes. When keratinocytes leave the basal layer, they begin to undergo terminal differentiation. When they reach the granular layer, the concentration of calcium ions inside the keratinocytes rises, resulting in activation of transglutaminase. The envelope precursor proteins, which at this stage are located just beneath the plasma membrane, are crosslinked by transglutaminase (Rice and Green (1979), ibid.; Greenberg et al. (1991) *FASEB*, 5:3071–3077) and the resulting envelope becomes thoroughly insoluble, even in the presence of detergents and reducing agents (Green (1977), *Cell*, 11:405–416; Hohl (1990), *Dermatologica*, 180:201–211). This envelope is the most resistant structure of the skin since keratin filaments, even though they are stabilized by disulfide bonds, can be dissolved by a combination of detergent and reducing agent. Transglutaminase and its crosslinked products are also present in hair and nails (Rice et al., *Keratinocyte Handbook*, (in press)).

SUMMARY OF THE INVENTION

The invention comprises a composition suitable for topical application to mammalian skin, hair and/or nails comprising a corneocyte protein, or polypeptide fragment thereof. The proteins or polypeptides are dispersed in a cosmetically acceptable vehicle which is designed to permit effective application of the proteins or polypeptides to the skin, hair or nails. A method for forming a protective layer on mammalian skin, hair or nails by applying a topical cosmetic composition containing an effective amount of the proteins or polypeptides also is the subject of the present invention.

The composition alternatively may comprise a crosslinking agent which is specific for corneocyte proteins, i.e., which forms crosslinks or induces crosslinking between corneocyte proteins already present in the stratum corneum. The crosslinking agent may be a chemical agent which reacts with two or more functional groups present in amino acid side chains of the proteins thereby forming crosslinks between the amino acids of different proteins. Chemical crosslinkers, such as glutaraldehyde, typically are themselves incorporated into the crosslink. Alternatively, the crosslinking agent may be an enzyme, such as transglutaminase, which induces formation of crosslinks between glutamine and lysine residues of adjacent polypeptides.

Corneocyte proteins which are preferred for use in the present composition and method include involucrin, loricrin, cornifin, trichohyalin, sciellin, profilaggrin and keratolinin and/or polypeptide fragments of these proteins. The proteins or polypeptides may be natural-sourced or recombinant. The proteins or polypeptides may be crosslinked, if desired, using a chemical crosslinker or an enzyme which forms bonds between adjacent polypeptides. Optionally, the proteins or polypeptides may be modified, for example, by chemically derivatizing or substituting one or more of the amino acids in the protein or polypeptide chain. Such modifications can be designed to impart specific properties to the protein or polypeptide for a selected application.

In a preferred embodiment, a protective layer is formed on skin, hair or nails by applying thereto a composition containing one or more corneocyte proteins or polypeptides. The proteins or polypeptides may be crosslinked to form the protective layer. For this purpose, a crosslinking agent capable of inducing formation of isopeptide bonds between molecules of the protein or polypeptide preferably is included in the composition. In another embodiment, a composition comprising only the crosslinking agent is applied, thereby inducing crosslinking of proteins already present in the skin, hair or nails. The presence of the crosslinking agent induces formation of a crosslinked protein network analogous to the corneocyte envelope which occurs naturally in skin. The protein network forms a protective layer on the skin, hair or nails which can help protect the skin, hair or nails from physical, environmental or chemical injury. Specific protectants, such as moisturizers or sunscreens, optionally may be included in the cosmetic composition.

BRIEF DESCRIPTION OF THE FIGURES

FIG. 1 is a graph illustrating the preferential crosslinking of involucrin to particulates in which FIG. 1A is a comparison of crosslinking of cytosolic proteins of fibroblasts (solid circles) and keratinocytes (open triangles); and FIG. 1B is a comparison of crosslinking of cytosolic proteins of keratinocytes (open triangles) and of involucrin (open circles).

DETAILED DESCRIPTION

Figure 1:
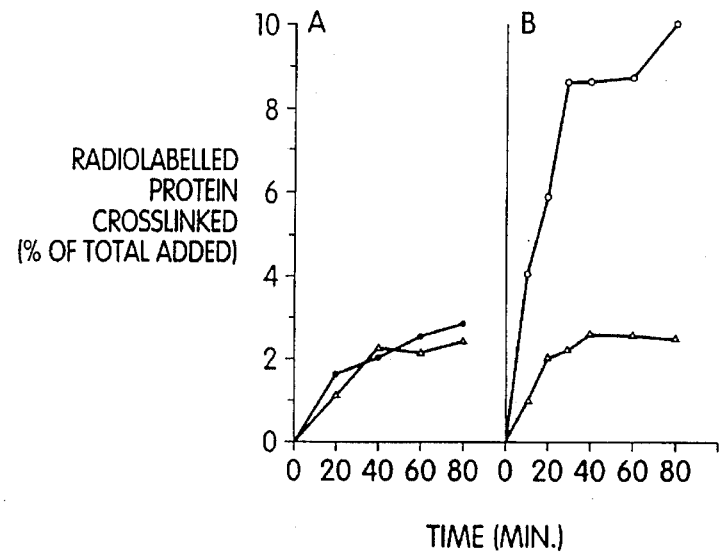

Proteins which are useful in the present composition and method comprise corneocyte proteins and polypeptide fragments thereof. Corneocyte proteins which are presently preferred include, for example, involucrin, loricrin, cornifin, trichohyalin, sciellin, profilaggrin and keratolinin. Involucrin has been described, for example, by Rice and Green (1979), ibid.; and Banks-Schlegel and Green (1981) *J. Cell*

Biol., 90:732–737. Loricrin has been described, for example, by Mehrel et al. (1990) *Cell*, 61:1103–1112; and Steven et al. (1990) *J. Struct. Biol.*, 104:150–162. Cornifin has been described, for example, by Marvin et al. (1992) *PNAS*, 89:11026–11030. Trichohyalin has been described, for example, by Fietz (1990) *J. Cell Biol.*, 110:427–436. Sciellin has been described, for example, by Kvedar et al. (1992) *Differentiation*, 49:195–204. Profilaggrin has been described, for example, by Markova et al. (1993) *Mol. and Cell Biol.*, 13:613–625. Keratolinin has been described, for example, by Zettergren et al. (1982) *PNAS*, 81:238–242. Natural-sourced or recombinant proteins or polypeptides can be used.

The composition comprises an effective amount of one or more corneocyte proteins or polypeptides in a cosmetically acceptable vehicle. The composition is formulated to be suitable for topical application to mammalian skin, hair and/or nails. In a preferred embodiment, the composition further comprises a crosslinking agent. The crosslinking agent can be a chemical crosslinking agent, e.g., a difunctional or multifunctional compound having functional groups capable of forming ionic or covalent bonds with amino acids in the polypeptide chain. The crosslinking agent can also be an enzyme which is capable of inducing formation of bonds between molecules of the protein or polypeptide. Enzymes are preferred agents for this purpose. A particularly preferred enzyme is calcium-activated keratinocyte transglutaminase (hereinafter, "transglutaminase") which forms isopeptide bonds between glutaminyl and lysyl residues of adjacent polypeptides. Transglutaminase preferably is added to the composition together with a concentration of calcium ions sufficient to render the enzyme enzymatically active. Corneocyte proteins applied to skin, hair or nails together with or following transglutaminase will be crosslinked to the outer layers of the skin, hair or nails, thereby forming the protective layer, or enhancing the protective properties of the stratum corneum.

In another preferred embodiment of the present invention, a composition comprising transglutaminase is applied to skin, hair or nails. The transglutaminase composition preferably contains a source of calcium ions to activate the enzyme. Alternatively, calcium ions may be applied subsequent to application of the transglutaminase composition. Application of transglutaminase and its activation by the calcium ions crosslinks corneocyte proteins which are present in the stratum corneum of the skin, hair or nails, thereby resulting in formation of the desired crosslinked layer.

Transglutaminase and the envelope precursor proteins can be extracted from natural sources; however, it is preferable to produce them by expression of the encoding cDNA's in suitable host cells. Various hosts have been used to produce recombinant proteins, e.g., bacterial cells, yeast, mammalian cells or insect cells infected with recombinant baculovirus. Genes encoding the corneocyte proteins are available. For example, complementary DNA (cDNA) encoding human involucrin (Eckert and Green, (1986) *Cell*, 46:583–589), human loricrin (Hohl et al. (1991) *J. Biol. Chem.*, 266:6626–6636), and human cornifin (Marvin et al., ibid.) have been isolated and sequenced. The cDNA encoding human keratinocyte transglutaminase has been described by Phillips et al. (1990) *PNAS, USA*, 87:9333–9337.

Baculovirus is the currently preferred host for producing the present proteins. Baculovirus seems to offer the highest levels of recombinant protein production together with correct processing of the protein, if necessary. Methods of producing recombinant proteins using baculoviruses are described, for example, by Piwnica-Worms in *Current Protocols in Molecular Biology*, Sections 16.8 through 16.11, John Wiley and Sons, New York, N.Y. (1990). The most widely used baculovirus for expression of cDNA's is *Autographa Californica*, and is commercially available from Invitrogen Corp., San Diego, Calif. In this system, the cDNA's are subcloned into the baculovirus transfer vector in the polyhedrin gene. SF9 or SF21 insect cells are cotransfected with the recombinant transfer vector and wild-type vital DNA. Five to ten percent of the transfer vector undergoes homologous recombination with the wild-type virus as shown by morphology of plaques. Recombinant plaques are isolated and the virus is grown on a large scale. Genes expressed under control of the viral polyhedrin promoter can account for more than half the total cell protein, and production rates of recombinant protein have been reported to range from 1 mg to 500 mg/l of culture (Piwnica-Worms (1990), ibid). The recombinant proteins produced by this method can be purified, for example, by gel filtration and ion exchange chromatography.

The proteins or polypeptides may be modified, if desired. Such modifications may include, for example, chemically derivatizing one or more amino acids or altering the amino acid sequence of the protein or peptide. These modifications can be used to impart selected qualities to the proteins or polypeptides, e.g., to render them more water-soluble, or more resistant to chemical, environmental or enzymatic attack. For example, selected amino acid functional groups can be derivatized and/or crosslinked, thereby increasing the resistance of the protein to degradation.

The amount of corneocyte proteins or polypeptides in the composition is the amount sufficient to provide a protective layer on the skin, hair or nails. The amount will vary depending on the formulation and the performance desired. In general, an amount of from about 0.1% to about 90% by weight protein or polypeptide will be sufficient for most purposes. Where the composition comprises only the crosslinking agent, the amount of crosslinking agent included in the composition will be an amount sufficient to induce formation of crosslinks between corneocyte proteins which are present in the stratum corneum. When transglutaminase is used, a source of calcium ions also must be applied either together with or subsequent to application of the enzyme.

The composition containing the proteins or polypeptides further comprises a cosmetically acceptable vehicle which is suitable for topical application to skin, hair and/or nails. For this purpose, the composition may comprise ingredients adapted to form a cream, gel, emulsion, liquid, suspension, nail coating, skin oil or lotion, for example. Ingredients which may be included in the composition include, for example, moisturizing agents, astringent agents, film-forming materials, surfactants, emollients, humectants, moisturizers, sunscreens, pigments or other proteins and/or fibers. Examples of such ingredients include various hydroxylated compounds, such as monomeric glycols, e.g., propylene glycol, ethyl alcohol, glycerin and butylene glycol, polymeric moisturizers such as polyglycerylmethacrylate, derivatives of palmitates and stearates, triglycerides of fatty acids, lanolin, vegetable or mineral oils, and waxes.

The nature of the vehicle will depend upon the method chosen for topical administration of the composition. The vehicle can itself be inert or it can possess physiological or pharmaceutical benefits of its own. The selection of a vehicle for this purpose presents a wide range of possibilities depending on the desired product form of the composition.

For purposes of the present invention, vehicles are substances which can act as diluents, dispersants, or solvents for the proteins or polypeptides Which ensure that they can be applied to and distributed evenly over the skin, hair and/or nails at an appropriate concentration. The vehicle is preferably one which can aid formation of a protective layer on the skin. The vehicle or vehicles can comprise from 1 to 99.9%, preferably from 50 to 99.5% and ideally from 90 to 99% by weight of the compositions.

Emollients which may be used in the composition include, for example, stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polthylene glycol, triethylene glycol, lanolin, sesame oil, coconut oil, arrachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate.

Humectants which may be used include, for example, glycerin, sorbitol, sodium 2-pyrrolidone-5-carboxylate, soluble collagen, dibutylphthalate, gelatin.

Film-forming materials may include, for example, acrylic polymers, nitrocellulose polymers, ethyl acetate resins, butyl acetate resins, toluenesulfonamide resins, formaldehyde resins, polyvinylbutyral resins, polyester resins, and various other polymers and copolymers.

Pigments may include, for example, titanium dioxide, micas, iron oxides, barium lake, calcium lake, aluminum lake, bismuth oxychloride, zirconium lake and calcium oxides.

Other materials which can be used in the present compositions include solvents, thickeners and powders. Examples of each of these, are as follows:

Solvents may include water, ethyl alcohol, toluene, methylene chloride, isopropanol, n-butyl alcohol, castor oil, ethylene glycol monoethyl ether, diethylene glycol monobutyl ether, diethylene glycol monoethyl ether, dimethyl sulphoxide, dimethyl formamide and tetrahydrofuran.

Thickeners may include starch, gums such as gum arabic, kaolin or other clays, hydrated aluminum silicate, fumed silica, carboxyvinyl polymer, sodium carboxymethyl cellulose or other cellulose derivatives, ethylene glycol monostearate and sodium alginates.

Powders may include chalk, talc, fullers earth, colloidal silicon dioxide, sodium polyacrylate, tetra alkyl and/or trialkyl aryl ammonium smectites and chemically modified magnesium aluminum silicate.

The composition according to the invention optionally may comprise a perfume in an amount sufficient to make the composition acceptable to the consumer and pleasant to use. Usually, the perfume will form from about 0.01 to 10% by weight of the composition.

A protein stabilizing agent may be included in the composition. For example, skin contains natural proteases which might at least partially degrade the protein. Therefore, the presence of protein stabilizing agent such as a protease inhibitor can protect the protein. Examples of protein stabilizing agents include, for example, glycerol, ethylenediaminetetraacetic acid, cysteine, and proteinase inhibitors such as $\alpha_2$-macroglobulin, $\alpha_1$-antitrypsin, leupeptin, pepstatin, antipain, and cystatin. Cystatin is naturally present in epidermis and may be particularly useful for this purpose.

The present compositions preferably comprise one or more surfactants. The term "surfactants" refers to surface active agents which, when added to water, cause it to penetrate more easily into, or spread on the surface of another material, by reducing the surface tension of the water at the water-air or water-oil interface. By "surface active agent" is meant any compound that reduces surface tension when dissolved in water or water solutions.

The selection of a surfactant for this purpose presents a wide range of possibilities known in the art. Preferred examples of surface active agents include the following:

(i) Anionic surfactants, such as metallic or alkanolamine salts of fatty acids for example sodium laurate and triethanolamine oleate;

alkyl benzene sulphones, for example triethanolamine dodecyl benzene sulphonate;

alkyl sulphates, for example sodium lauryl sulphate;

alkyl ether sulphates, for example sodium lauryl ether sulphate (2 to 8 EO);

sulphosuccinates, for example sodium dioctyl sulphonsuccinate;

monoglyceride sulphates, for example sodium glyceryl monostearate monosulphate;

isothionates, for example sodium isothionate;

methyl taurides, for example Igepon T;

acylsarcosinates, for example sodium myristyl sarcosinate;

acyl peptides, for example Maypons and lamepons; acyl lactylates, polyalkoxylated ether glycollates, for example trideceth-7 carboxylic acid;

phosphates, for example sodium dilauryl phosphate.

(ii) Cationic surfactants, such as amine salts, for example sapamin hydrochloride;

quartenary ammonium salts, for example Quaternium 5, Quaternium 31 and Quaternium 18;

(iii) Amphoteric surfactants, such as imidazol compounds, for example Miranol;

N-alkyl amino acids, such as sodium cocaminopropionate and asparagine derivatives;

betaines, for example cocamidopropylebetaine (iv) Nonionic surfactants, such as fatty acid alkanolamides, for example oleic ethanolamide; esters or polyalcohols, for example Span; polyglycerol esters, for example that esterified with $C_12_{-1}8$ fatty acids and one or several OH groups;

Polyalkoxylated derivatives, for example polyoxy:polyoxyethylene stearate;

ethers, for example polyoxyethe lauryl ether;

ester ethers, for example Tween;

amine oxides, for example coconut and dodecyl dimethyl amine oxides. Mixtures of two or more of the above surfactants can be employed in the composition according to the invention.

The compositions of this invention may include a skin-structuring protein component. The term "skin-structuring protein" as used herein is intended to include natural proteins derived from animal or marine sources, as opposed to plant or vegetable sources, and which are substantive to the skin. Such animal proteins include, for example, high molecular weight glycoproteins, such as the fibronectins. Other useful animal proteins include soluble collagen, hydrolyzed animal collagen, keratins, striated muscle fiber or an extract thereof, hydrolyzed or partially hydrolyzed elastin, hydrolyzed silk, and soluble reticulin. The skin-structuring protein component can comprise a mixture, as well as a single protein product.

The skin care compositions within the scope of this invention may include one or more astringent agents. Such agents include, for example, arnica flowers or extracts thereof, lower alkyl alcohols, witch hazel, boric acid, lactic acid, methol, camphor, zinc phenol sulphonate, aluminum acetate, aluminum sulfate, and zinc chloride or sulfate. For many purposes, a natural product, e.g., arnica extract, is preferred, especially in combination with a proteinaceous material, such as hydrolyzed marine protein and/or a vegetable protein as can be extracted from barley and other grains, for example.

The compositions of this invention may include a cellulosic film-former, if desired. Cellulosic film-formers include polysaccharides such as chitin, which can be obtained from marine sources. The chemical structure of the cellulosic film-former component is distinguished from that of the mucopolysaccharide component in predominantly containing monosaccharide repeating units, N-acetyl-D-glucosamine in the case of chitin.

If desired, the composition may contain UV-A and UV-B radiation filters, sunscreens, free-radical blockers, vitamin extracts, and antioxidants.

In addition to the elements described above, the skin care compositions of this invention may include cosmetically acceptable preservatives, antiseptics, pigments or colorants, fragrances, masking agents, and carriers, such as water and lower alkyl, e.g., $C_1$-$C_4$, alcohols, including ingredients to control the viscosity of the compositions.

Compositions in the form of hair dressing lotions may incorporate anionic, nonionic or cationic polymers in an aqueous, alcoholic or aqueous/alcoholic solution.

The quantities of the various ingredients in a composition within the scope of this invention can be varied over a wide range, it only being necessary that cosmetically effective amounts be present. In general, the primary moisturizing agent may comprise between about 0.25 and about 10 percent, desirably between about 0.3 and about 5 percent, by weight of the composition. The skin-structuring protein may comprise between about 0.05 and about 8 percent, desirably between about 0.05 and about 2.0 percent, by weight of the composition. The astringent agent, e.g., arnica combined with marine and vegetable protein, may comprise between about 0.1 and about 5 percent, preferably between about 0.1 and about 0.25 percent, by weight of the composition.

The present composition containing the proteins can be applied to the skin, hair and/or nails of humans in any of several different ways. For example, a composition containing the substrate proteins could be applied and, if crosslinking is desired, the enzyme (with calcium ions, if necessary) could be applied subsequently. Alternatively, the crosslinking agent may be added to the composition prior to its application. In another embodiment, the composition could be applied as an emulsion in which the enzyme (and the calcium ions) are held separate from the protein substrates in different phases and the two reagents are combined upon application to the skin or hair as the droplets containing each fuse and their contents become mixed. In yet another embodiment, a composition containing a crosslinker specific for corneocyte proteins is applied to the skin, hair or nails, thereby inducing crosslinking of corneocyte proteins already present in the stratum corneum of the skin, hair or nails. If transglutaminase is used, a source of calcium ions is applied together with or subsequent to application of the enzyme.

The present compositions and methods provide cosmetic compositions capable of forming a protective layer on skin, hair or nails which can mimic, or enhance the protective ability of the stratum corneum of natural skin. The use of corneocyte proteins which are naturally present in skin, hair and nails, particularly in a crosslinked state, permits a resistant layer to form which can protect skin and hair from environmental damage. The present corneocyte protein compositions may be applied as a cream or lotion, shampoo or hair gel, nail polish or coating or may be included in a foundation make-up formula, for example. Exemplary formulations for such cosmetic compositions are readily available, for example, in the Formulary section of the "happi" (household and personal products industry) journal, and other sources well known to those skilled in the art.

The invention is further illustrated by the following Exemplification.

EXEMPLIFICATION

In the following example, involucrin is extracted from human keratinocytes, purified, and tested for the ability to become crosslinked to a particulate fraction (from Simon and Green (1985) *Cell*,40:677–683).

Involucrin and Other Cytosolic Proteins Compared as Substrates for Crosslinking to Keratinocyte Particulates Cultured keratinocytes and fibroblasts were grown in the presence of [$^{35}$S]labeled methionine, and a crude extract containing cytosolic proteins was prepared from each cell type. The extract prepared from keratinocytes was passed through an immune affinity column to remove involucrin. After incubation of the labeled cytosolic proteins or of involucrin with unlabeled keratinocyte particulates under conditions permitting cross-linking, the particulates were centrifuged, washed twice with preparation buffer, and once with a solution of 2% SDS and 5% mercaptoethanol. The pellet was suspended in buffer and applied to the sample chamber of a gel electrophoresis apparatus. After electrophoresis to remove any residual uncrosslinked proteins, the top of the gel was cut out and counted. The keratinocyte particulates were able to incorporate labeled cytosolic proteins of either cell type with about the same efficiency (FIG. 1A). Within 1 hr, about 2% of the total labeled protein was cross-linked to the particulate fraction.

The labeled involucrin-free cytosol of keratinocytes was then compared with purified labeled involucrin for ability to become crosslinked to keratinocyte particulates (FIG. 1B). The involucrin was initially 4–5 times more effective, and 10% became crosslinked into aggregates within 80 min. Fibroblast particulates and mixtures of fibroblast particulates and cytosol were incapable of crosslinking involucrin into SDS-insoluble polymers.

Figure 2:
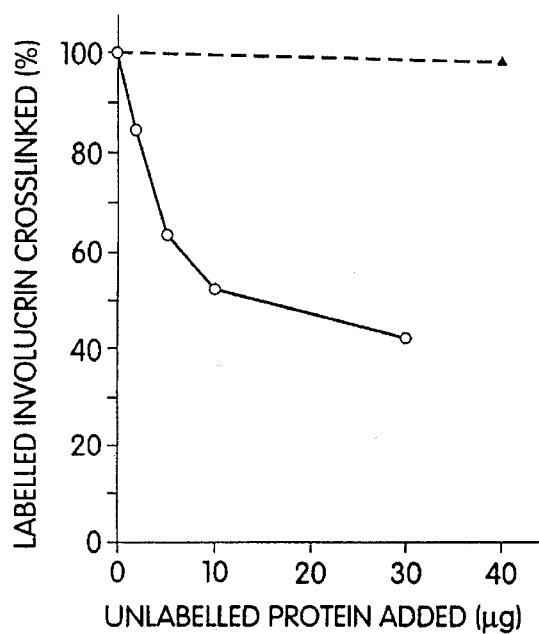
FIG. 2 is a graph illustrating the inability of other cytosolic proteins to compete with involucrin in crosslinking to particulates; keratinocyte particles were incubated with increasing amounts of unlabeled involucrin (circles) and unlabeled involucrin-free cytosol (triangles).

While involucrin was preferred to other cytosolic proteins in the crosslinking to particulates, the preference factor was smaller than that observed for putrescine labeling. It was therefore of interest to determine whether unlabeled cytosolic proteins were able to compete with involucrin in the cross-linking. Keratinocyte particulates were incubated with [$^{35}$S]involucrin and with unlabeled involucrin or involucrin-free cytosolic protein. As seen in FIG. 2, unlabeled involucrin effectively competed with labeled involucrin, reducing the formation of labeled product by over 50%. A higher concentration of involucrin-free cytosol exerted no significant reduction in cross-linking of labeled involucrin.

Formation of Smaller Aggregates Containing Polymerized Involucrin

The cross-linking of involucrin into large aggregates may take place in stages. When keratinocyte particulates were incubated with [$^{35}$S]involucrin for 30 min, they were found to form involucrin-containing polymers of different sizes. Some of these polymers remained soluble and were separated from the particulates by centrifugation for 15 min at 15,000×g. When subjected to electrophoresis, the supernatant containing these polymers gave bands corresponding to approximate molecular weights of 200 kd and 300 kd. The smaller polymer was generally more abundant. These proteins (Type 1 polymers) may be homopolymers of involucrin.

Figure 3:
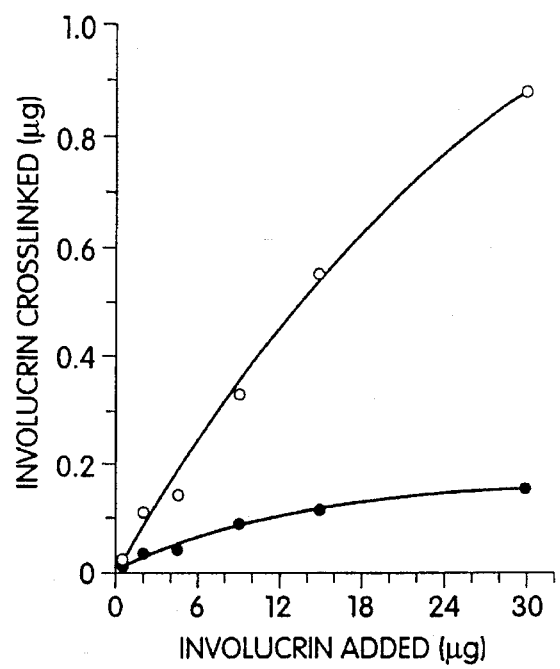
FIG. 3 is a graph illustrating the detergent solubility of crosslinked involucrin attached to keratinocyte particles; keratinocyte particles were incubated under crosslinking conditions with increasing amounts of involucrin then boiled in sodium dodecyl sulfate (SDS). The soluble type II polymers are shown as solid circles and insoluble type III polymers as open circles.

In the centrifuged particulates, there were two other kinds of polymers. When extracted with a solution containing 2% SDS and 5% mercaptoethanol at 100° C. and recentrifuged, Type II polymers became soluble, and Type III polymers remained large enough to be sedimentable. Type II polymers had molecular weights greater than 400 kd, as they did not enter a 5% acrylamide gel even after electrophoresis for 4 hr. The proportion of crosslinked involucrin in polymers of Types II and III depended on the concentration of involucrin. At low concentrations, 30–50% of labeled involucrin polymers were of Type II (FIG. 3). At higher concentrations of labeled involucrin, nearly all polymers were of Type III. This suggests that the Type II polymers may be precursors of the Type III.

The Role of Involucrin in the CrossLinking of Particulates

When transglutaminase is activated in intact keratinocytes by the introduction of $Ca^{++}$ not only involucrin but also proteins resident in the cell membrane become cross-linked (Simon and Green (1984) *Cell*,36:827–834). In order to test for a role of involucrin in the crosslinking of these proteins, the effect of involucrin on the crosslinking in vitro of proteins of the particulate fraction was examined.

Cultured keratinocytes were grown in the presence of [$^{35}$S]labeled methionine, and the labeled particulate fraction was isolated. This fraction was then incubated under crosslinking conditions, and the incorporation of label into SDS-insoluble cross-linked material was measured (Table 1). An appreciable background of crosslinked material was present prior to incubation; this crosslinking took place during cultivation, when some crosslinked envelopes form spontaneously, the number increasing with the age of the culture. During incubation of the particulate fraction under crosslinking conditions, more labeled protein became crosslinked. Addition of involucrin to the labeled particulates produced a further increase in the amount of labeled protein crosslinked. The addition of involucrin-free cytosolic protein at the same concentration (or up to 25-fold higher concentration) had no such effect. This shows that while soluble proteins other than involucrin may crosslink to proteins of the particulate fraction, the average cytosolic protein does not share the specific ability of involucrin to promote the crosslinking of particulate proteins.

Discussion

As shown earlier, the crosslinked envelope of the keratinocyte appears to be assembled from a mixture of membrane bound and cytosolic constituents (Rice and Green (1979) *Cell*,18:681–694; Simon and Green (1984) ibid). Because of the difficulty in obtaining a pure membrane fraction from keratinocytes, the assays used in this study employed crude particulates. However, proteins present in the particulates and subject to cross-linking have been shown to be membrane associated (Simon and Green (1985) ibid).

As demonstrated here, the particulate fraction of keratinocytes, but not a similar fraction prepared from fibroblasts, is able to crosslink cytosolic protein to make aggregates in vitro. This difference between the two cell types is correlated with the fact that the transglutaminase of keratinocytes is predominantly linked to particulates (Thacher and Rice (1983) *Fed. Proc.*, 42(7):1925 Abstr. 980), whereas that of fibroblasts is predominantly cytosolic. The correlation is rendered still more significant by the finding that keratinocytes possess a transglutaminase different from that of fibroblasts or other cell types (Phillips et al. (1990) *PNAS*, 87:9333–9337). It is assumed that any cytosolic protein rendered insoluble in SDS and unable to enter polacrylamide gels is crosslinked to proteins within the particulate fraction. As shown earlier, membrane proteins of 195 kd and 210 kd became crosslinked in intact cells rendered permeable to $Ca^{++}$ (Simon and Green (1984) ibid); over 50% of each of these proteins also became SDS-insoluble in the reconstituted system described here.

Transglutaminase is able to couple putrescine and other amines to monomeric protein (Clark et al. (1950) *Arch. Biochem. Phys.*,79:338–354; Folk and Chung (1973) *Adv. Enzymol.*,38:109–191). Indeed, it was by its ability to act as an amine acceptor in the presence of cytosolic enzyme that involucrin was first identified (Rice and Green (1979) ibid). The present study shows that the particulate fraction of keratinocytes is much more effective than the cytosol in catalyzing amine labeling of involucrin. In the reaction with putrescine, the particulate transglutaminase preferred, as a substrate, involucrin to the average cytosolic protein by a factor of at least 80-fold. This is probably an underestimate, since some of the putrescine-labeled involucrin was probably crosslinked into aggregates and escaped detection. It was known from amino acid analysis of involucrin that 45% of all residues consisted of glutamic acid of glutamine (Rice and Green (1979) ibid). Other studies have shown that in at least part of the involucrin molecule, glutamine alone accounts for about 25% of the residues. Nearly 15% of involucrin is composed of leucine residues, known to be important neighbors of crosslinking glutamine residues in casein and model substrates (Gorman and Folk (1984) *J. Biol. Chem.*,259:9007–9010). It is perhaps for these reasons that involucrin is a better transglutaminase substrate than most other proteins.

When keratinocyte particulates were tested for ability to discriminate between involucrin and other cytosolic proteins in crosslinking to form large SDS-insoluble aggregates, they preferred involucrin to other proteins, but by a factor of only 5 or less. There are several possible explanations for the relatively low figure. One is that in vitro, the involucrin may not be properly located with respect to particulate proteins to which it must crosslink, and the true selectivity of the system is not expressed. A second possibility is that involucrin is subject to proteolysis in vitro, particularly in the presence of $Ca^{++}$ and free SH groups, both of which are required for transglutaminase activity. After the incubation under crosslinking conditions, residual soluble involucrin frequently gives a diffuse band in gel electrophoresis. Intactness of the molecule may be more important for crosslinking of the protein to particulates than for its ability to act as putrescine acceptor. Finally, although its ability to couple to putrescine shows that involucrin acts as an amine acceptor in forming the isopeptide bond, other cytosolic proteins may act as amine donors. Consistent with this possibility is the fact that in cross-linking to particulates, other cytosolic proteins are ineffective as competitors against labeled involucrin (FIG. 2).

The total concentration of all cytosolic proteins in the keratinocyte is about 25 times higher than that of involucrin. If the preference factor for involucrin in cellular crosslinking were only 5-fold, it might be expected that involucrin would account for only about 20% of the cytosolic contribution to the crosslinked envelope. However the crosslinking of cytosolic proteins by keratinocyte particulates in vitro is saturated at a protein concentration of about 5 mg/ml, (much lower than the cellular cytosolic protein concentration of about 65 mg/ml). Even though a maximal rate of crosslinking was not reached at the highest involucrin concentration tested in vitro (0.6 mg/ml), the amount of involucrin crosslinked was equal to the saturating value for all other cytosolic proteins. If the proportion of involucrin and other cytosolic proteins crosslinked in vitro reflects their behavior in the intact cell, the contribution of involucrin to the envelope would not be less than 50% of the total cytosolic contribution.

In the keratinocyte, the crosslinking system has evolved considerably to form the substantial envelope that underlies the plasma membrane in the final stage of terminal differentiation. The cytosolic protein involucrin not only contributes to the mass of the envelope but also promotes the polymerization of other proteins likely to be associated with the plasma membrane. Other cytosolic proteins are not able to substitute for involucrin in this function (Table 1). In this way, involucrin may also aid in securing the envelope to the plasma membrane.

TABLE 1

Crosslinking of Proteins of the Particulate Fraction In Vitro and the Effect of Involucrin % of Total [$^{35}$S] in Form of Polymer after Incubation In Vitro

| Experiment # | Background* | No Added Protein | +Involucrin-free cytosolic protein (2.0 µg) | +Involucrin 2.0 µg |
|---|---|---|---|---|
| 1 | 4.4 | 7.2 | 7.0 | 11.8 |
| 2 | 2.0 | 9.3 | 9.2 | 12.5 |
| 3 | 0.4 | 8.8 | 8.7 | 11.0 |
| 4 | 0.8 | 10.4 | 10.5 | 12.9 |
| 5 | 1.9 | 7.4 |  | 10.7 |

*Polymerized in intact cells prior to incubation.

A particulate fraction, prepared from labeled keratinocytes and containing 50 µg of protein, was incubated for 30 min under cross-linking conditions. After the reaction was terminated, the particulates were washed, first with preparation buffer, and then with a solution of SDS containing mercaptoethanol. Any remaining unpolmerized material was removed by electrophoresis, and the polymers remaining in the stacking gel were counted. Controls incubated in the presence of either EDTA or cystamine showed no increase over background.

Methods and Materials

Cell Culture

Human epidermal keratinocytes (strain N) were grown in the presence of lethally irradiated 3T3 cells (Rheinwald and Green (1975) *Cell*, 6:317–330) using a 3:1 mixture of the Dulbecco-Vogt modification of Eagle's medium and Ham's F-12 medium (Ham (1965) *Proc. Natl. Acad. Sci. USA*, 53:288–293). Supplements were as follows: fetal calf serum, 10%; hydrocortisone, 0.4 µg/ml; insulin, 5 µg/ml; transferrin, 5 µg/ml; triiodothyronine, $2\times10^{-9}$M; choleragen, $10^{-10}$M; and adenine, $1.8\times10^{-4}$M (Peehl and Ham (1980) *In Vitro*, 16:526–538; Wu et al. (1982) *Cell*, 31:693–703. Beginning 3 days after inoculation, epidermal growth factor (EGF) prepared according to Savage and Cohen (1972) (*J. Biol. Chem.*, 247:7609–7611) was added to the medium to 10 ng/ml (Rheinwald and Green (1977) (*Nature*, 265:421–424). Human fibroblasts and 3T3 cells were grown in Dulbecco-Vogt modification of Eagle's medium supplemented with 10% fetal calf serum or 10% calf serum, respectively. All cultures were incubated at 37° C. in an atmosphere containing 10% $CO_2$, and the medium was changed twice weekly.

Preparation of Particulates and Cytosol

Keratinocytes or fibroblasts grown to confluence were washed twice with ice cold 0.6 mM HEPES, pH 7.4; 0.15 M NaCl; 0.4 mg/ml bovine serum albumin; 0.2 mM phenymethyl sulfonyl fluoride (PMSF); 10 mM ξ-amino caproic acid; 10 mM phenymethyl sulfonyl fluoride (PMSF); 10 mM EDTA; and 1 mM $MgCl_2$. The suspension was then sonically disintegrated with 5 bursts at a setting of 6 on a Branson Sonifier, and the particulates and cytosol were separated by centrifugation for 30 min at 1000,000×g. The fibroblast and keratinocyte particulates were then washed twice with the preparation buffer, centrifuging for 15 min at 30,000×g and 15,000×g, respectively.

Protein Purification and Antiserum Production

Involucrin was purified either according to the procedure of Rice and Green (1979) ibid, or Etoh et al. (1986) *Biochem. Biophys. Res. Comm.*, 136:51–56. Protein concentration was measured by the procedure of Lowry et al. (1951), *J. Biol. Chem.*, 193:265–275). Batches of involucrin prepared by the two methods were indistinguishable.

To prepare antiserum 100 µg of involucrin was dissolved in isotonic buffer containing 50% Freund's complete adjuvant and injected intradermally into rabbits. Booster injections, containing 50 µg of involucrin in 50% Freund's incomplete adjuvant, were given every 4 weeks thereafter. Animals were bled from the ear 1 week after each booster injection.

Preparation of Involucrin-Free Cytosol

Involucrin-free cytosol was obtained by affinity chromatography using a column of anti-involucrin antibody coupled to Sepharose 4B (Pharmacia). An immunoglobulin fraction was first prepared by precipitating the involucrin antiserum with ammonium sulfate at 40% saturation. The precipitated immunoglobulin fraction was dialyzed 3 times against 1 liter of isotonic phosphate buffer. The antibodies specific for involucrin were then obtained by affinity chromatography using a column of Sepharose 4B coupled in involucrin. The is column was prepared use 300 µg of involucrin dissolved in 1.5 ml of 0.1M sodium bicarbonate and dialyzed against a solution containing 0.1M sodium bicarbonate and 0.5M sodium chloride. The involucrin solution was then added to 0.3 g of CNBr-activated Sepharose, and the coupling was carried out according to the manufacturer's recommendations. 1.0 ml of the immunoglobulin fraction obtained from involucrin antiserum was added in a 1.0 ml volume to a column of involucrin-Sepharose. The column was then washed with 6 volumes of 20 mM Tris-HCl, pH 7.5, containing 0.5M NaCl. No anti-involucrin antibody could be detected in this wash. The specifically bound antibody was then eluted with 0.1M glycine-HCl, pH 2.5. Immunoblot analysis of the eluate showed that 30% of the antibody activity was recovered. To prepare the anti-involucrin antibody column, the eluted antibody (213 µg) was neutralized with 1M NaOH within 10 mn and coupled to Sepharose as described above. Coupling was 67% effective.

To separate involucrin from other cytosolic proteins, unfractionated cytosol was added in a 0.5 ml volume to the column containing anti-involucrin antibody and the column was washed with preparation buffer. As determined by immunoblot analysis, this column was capable of removing greater than 99.98% of the involucrin contained in 1 mg of cytosolic protein. The involucrin was eluted from the column with 0.1M glycine-HCl, pH 2.5, and was neutralized.

Electrophoretic analysis of the eluate showed that the protein present in the involucrin band accounted for over 95% of the total.

CrossLinking Assays

All experiments were carried out at 37° C. in a reaction volume of 50 µl containing preparation buffer. Crosslinking was activated by the addition of $CaCl_2$ to a final concentration of 10 mM. Controls contained either 20 mM EDTA and no $CaCl_2$, or 20 mM cystamine.

Two types of assay were employed. The first measured the covalent crosslinking of [$^3$H]putrescine to protein (Folk and Cole, (1966) *Biochim. Biophys. Acta,* 122:244–264). No exogenous substrate (such as the commonly employed casein) was added; the acceptor protein was in all cases involucrin or other cellular proteins. In some experiments, incorporation of the putrescine into total trichloroacetic acid-precipitable material was determined. The precipitate was washed 4 times with 10% ice cold trichloroacetic acid, dissolved with sodium hydroxide, and reacidified with hydrochloric acid prior to counting. This assay measured both incorporation into aggregates, as well as soluble proteins. To measure incorporation into soluble proteins alone (either purified involucrin or a mixture of cytosolic proteins), the reaction products were electrophoresed, and the gels were fixed and washed in 10% acetic acid-methanol overnight. The gels were then either treated with Enhance (New England Nuclear), dried and fluorographed on X-OMat AR film at −70° C. to show labeling in discrete protein bands, or each separation lane was excised, incubated overnight at 37° C. in 3% Protosol in Econofluor (New England Nuclear), and counted.

The second crosslinking assay measured the formation of polymeric aggregates from labeled involucrin, labeled cytosolic proteins, or labeled particulate proteins. Following the reaction, the samples were centrifuged for 15 min and the pellet was washed twice in preparation buffer containing bovine serum albumin (BSA) and once with 2% SDS and 5% mercaptoethanol at 100%C. After the final centrifugation, the pellet was suspended in Laemmli sample buffer and any residual monomeric protein was removed by electrophoresis through a 5% polyacrylamide gel for about 4 hr at 30 mA. The stacking gel and the very top of the separating gel (1 mm) were cut out, treated with Protosol, and counted. As expected for a transglutaminase-catalyzed reaction (Clark et al. (1959) ibid; Folk and Chung (1973) ibid; Lorand et al. (1978) *J. Supramol. Struct.,* 9:427–440), crosslinking depended on the presence of calcium ions and was inhibited by cystamine, histamine, ethanolamine, or putrescine. The apparent $K_M$ of calcium, for each of these crosslinking reactions, was 0.1–0.2 mM.

Equivalents

Other embodiments of the present invention in addition to those specifically disclosed herein and which are equivalent thereto will be readily apparent to those skilled in the art. Such equivalents are intended to be encompassed within the scope of the following claims.

What is claimed is:

1. A cosmetic composition suitable for topical application to mammalian skin, hair or nails comprising:

(a) at least one corneocyte envelope protein in an amount sufficient to provide a protective layer on said skin, hair or nails;

(b) a transglutaminase in an amount sufficient to form covalent bonds between the corneocyte envelope protein and externally exposed corneocyte proteins present in the stratum corneum of said skin, hair or nails;

(c) calcium ions in an amount sufficient to activate the transglutaminase; and (d) a cosmetically acceptable vehicle, wherein the composition comprises an emulsion having two phases and wherein the corneocyte envelope protein is contained in one of the phases and the transglutaminase is contained within the other phase.

2. The composition of claim 1, wherein the corneocyte envelope proteins are selected from the group consisting of involucrin, loricrin, cornifin, trichohyalin, sciellin and profilaggrin.

3. The composition of claim 1, wherein the corneocyte envelope protein is a purified protein.

4. The composition of claim 1, wherein the corneocyte envelope protein is a human protein.

5. The composition of claim 1, wherein the corneocyte envelope protein is a recombinantly produced protein.

6. The composition of claim 1, wherein the transglutaminase is a human protein.

7. The composition of claim 6, wherein the transglutaminase is a purified protein.

8. The composition of claim 6, wherein the transglutaminase is a recombinant protein.

9. A method for providing a protective layer on mammalian skin, hair, or nails, said method comprising:

(A) applying to the skin, hair or nails:

(i) at least one corneocyte envelope protein in an amount sufficient to form said protective layer;

(ii) a transglutaminase in an amount sufficient to form covalent bonds between the corneocyte envelope protein and externally exposed proteins present in the stratum corneum of said skin, hair, or nails;

(iii) calcium ions in an amount sufficient to activate the transglutaminase; and (iv) a cosmetically acceptable vehicle;

wherein at least one of the members of the group selected from (i), (ii), and (iii) is kept separate from at least one of the other members of said group until ready for application; and (B) allowing the formation of said protective layer on said skin, hair, or nails after application of (i), (ii), (iii) and (iv).

10. The method of claim 9, wherein the corneocyte envelope proteins are selected from the group consisting of involucrin, loricrin, cornifin, trichohyalin, sciellin and profilaggrin.

11. The method of claim 9, wherein the corneocyte envelope protein is a purified protein.

12. The method of claim 9, wherein the corneocyte envelope protein is a human protein.

13. The method of claim 9, wherein the corneocyte envelope protein is a recombinantly produced protein.

14. The method of claim 9, wherein the transglutaminase is a human protein.

15. The method of claim 14, wherein the transglutaminase is a purified protein.

16. The method of claim 14, wherein the transglutaminase is a recombinant protein.

* * * * *

UNITED STATES PATENT AND TRADEMARK OFFICE
CERTIFICATE OF CORRECTION

PATENT NO. : 5,525,336

DATED : June 11, 1996

INVENTOR(S) : Howard Green and Philippe Djian

It is certified that error appears in the above-indentified patent and that said Letters Patent is hereby corrected as shown below:

On THE TITLE page, item 54,
On line 1, please replace the word "CORNEOCYTE" with --CORNEOCYTE--.

On the Title page, item 56,
IN THE OTHER PUBLICATIONS:
In the Markova reference, please replace the word "Epiderman" with --Epidermal--.

Column 4, line 10, please replace "vital" with --viral--.
Column 10, line 32, please replace "of" with --or--.
Column 13, lines 7 and 9, please replace "CaCl$_2$" with --CaCl$_2$--.

Signed and Sealed this

Twenty-first Day of January, 1997

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO.   : 5,525,336
DATED        : June 11, 1996
INVENTOR(S)  : Howard Green, et al It is certified that error appears in the above-identified patent and that said Letters Patent is hereby corrected as shown below:

On the title page, item [76], Inventors: "Dijan" should read -- Djian --.

Signed and Sealed this

Eighth Day of April, 1997

Attest:

BRUCE LEHMAN

*Attesting Officer*      *Commissioner of Patents and Trademarks*